US010383539B2

(12) United States Patent
Ibáñez Català et al.

(10) Patent No.: US 10,383,539 B2
(45) Date of Patent: Aug. 20, 2019

(54) SYSTEM AND METHODS FOR CLASSIFYING ARRHYTHMIA-RELATED HEARTBEATS

(71) Applicant: Smart Solutions Technologies, S.L., Madrid (ES)

(72) Inventors: Xavier Ibáñez Català, Valencia (ES); Silvia Ortín González, Mallorca (ES); Miguel Cornelles Soriano, Mallorca (ES); Claudio Rubén Mirasso Santos, Mallorca (ES)

(73) Assignee: Smart Solutions Technologies, S.L., Madrid (ES)

( * ) Notice: Subject to any disclaimer, the term of this patent is extended or adjusted under 35 U.S.C. 154(b) by 154 days.

(21) Appl. No.: 15/638,263

(22) Filed: Jun. 29, 2017

(65) Prior Publication Data
US 2018/0368723 A1    Dec. 27, 2018

(30) Foreign Application Priority Data

Jun. 22, 2017 (ES) .................................. 201730826

(51) Int. Cl.
| A61B 5/00 | (2006.01) |
| A61B 5/0452 | (2006.01) |
| A61B 5/0432 | (2006.01) |
| G06N 3/08 | (2006.01) |
| G06N 3/04 | (2006.01) |
| A61B 5/046 | (2006.01) |
| A61B 5/0464 | (2006.01) |
| A61B 5/0468 | (2006.01) |
| A61B 5/0245 | (2006.01) |
| A61B 5/04 | (2006.01) |

(52) U.S. Cl.
CPC .......... *A61B 5/04525* (2013.01); *A61B 5/046* (2013.01); *A61B 5/0432* (2013.01); *A61B 5/0464* (2013.01); *A61B 5/0468* (2013.01); *A61B 5/7267* (2013.01); *G06N 3/0445* (2013.01); *G06N 3/08* (2013.01); *A61B 5/0006* (2013.01); *A61B 5/0245* (2013.01); *A61B 5/04012* (2013.01)

(58) Field of Classification Search
CPC . A61B 5/04525; A61B 5/7267; A61B 5/0468; A61B 5/0464; A61B 5/046; A61B 5/0006; A61B 5/0432; A61B 5/04012; A61B 5/0245; G06N 3/08; G06N 3/0445
See application file for complete search history.

(56) References Cited

U.S. PATENT DOCUMENTS

| 2011/0105928 | A1* | 5/2011 | Bojovic | A61B 5/0006 600/515 |
| 2014/0128758 | A1* | 5/2014 | Galloway | A61B 5/7203 600/518 |
| 2015/0257668 | A1* | 9/2015 | Braojos Lopez | A61B 5/04012 600/512 |
| 2016/0135704 | A1* | 5/2016 | Zhang | A61B 5/04012 600/515 |

* cited by examiner

*Primary Examiner* — Scott M. Getzow
(74) *Attorney, Agent, or Firm* — Entralta P.C.; Justin G. Sanders; Peter D. Weinstein

(57) ABSTRACT

An arrhythmia detection system and associated methods are disclosed for analyzing and classifying arrhythmia-related heartbeats of a user based on an at least one biosignal associated with heart activity of the user, as captured by an at least one lead of an at least one ECG recording.

20 Claims, 5 Drawing Sheets

SYSTEM AND METHODS FOR CLASSIFYING ARRHYTHMIA-RELATED HEARTBEATS

RELATED APPLICATIONS

This application claims priority and is entitled to the filing date of ES application number 201730826—filed on Jun. 22, 2017. The contents of the aforementioned application are incorporated by reference herein.

BACKGROUND

The subject of this patent application relates generally to electrocardiography, and more particularly to a system and associated methods for classifying arrhythmia-related heartbeats based on extracted data from an at least one lead of an electrocardiogram recording.

Applicant(s) hereby incorporate herein by reference any and all patents and published patent applications cited or referred to in this application.

By way of background, electrocardiography is the process of recording the electrical activity of a patient's heart over a period of time using electrodes placed on the patient's skin. Electrodes on different parts of the body detect electrical impulses coming from different directions within the heart. In a standard twelve-lead electrocardiogram ("ECG"), the electrical activity of the heart is measured and recorded from twelve different angles (commonly referred to as "leads") across the body. The graph of voltage versus time produced by this non-invasive medical procedure is referred to as an electrocardiogram ("ECG" or "EKG"). The ECG is the most commonly used non-invasive tool to diagnose heart disease. It is also the standard method used to detect and diagnose arrhythmias, which are cardiac conditions caused by the abnormal electrical activity of the heart. Depending on the region of the origin of arrhythmias, they are broadly classified as either supraventricular or ventricular. The presence of transient, short-term or infrequent arrhythmias can only be detected by monitoring the electrical activity of the heart for long periods of time. Visual analysis of these long-term ECG recordings by a cardiologist tends to be very tedious and time-consuming. Thus, a major challenge is the development of an efficient decision support system capable of analyzing large volumes of recorded ECG data in a fast and efficient way, in order to aid in decision-making and informing patients as quickly as possible regarding potential treatment options.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing an arrhythmia detection system and associated methods for analyzing and classifying various types of arrhythmia-related heartbeats of a user—such as ventricular ectopic heartbeats—based on an at least one biosignal associated with heart activity of the user, as captured by an at least one lead of an at least one ECG recording. In at least one embodiment, the system includes an at least one computing device in selective communication with an at least one comparative database containing an at least one ECG recording representing a plurality of heartbeats, each said ECG recording comprising a temporal position and a beat class associated with each represented heartbeat. A real-time matrix, i.e. a matrix that can be updated in real time, is constructed corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat. The at least one lead is divided into a plurality of segments of a pre-determined temporal length. For each of the at least one segment, a beat matrix is defined, with each of an at least one row of said beat matrix representing a successive at least one heartbeat of said segment, and each of an at least one column of said beat matrix representing an at least one sample of said ECG recording taken around the temporal position of said at least one heartbeat. In at least one embodiment, the beat matrix is normalized such that all rows of said beat matrix have a mean of zero and a standard deviation of one. For each of the at least one heartbeat within said segment, a row for said heartbeat is added to the real-time matrix. A first column of the real-time matrix is populated with an interbeat interval between said heartbeat and an immediately preceding heartbeat. A second column of the real-time matrix is populated with an interbeat interval between said heartbeat and an immediately succeeding heartbeat. A third column of the real-time matrix is populated with an interval mean calculated over a pre-determined number of preceding heartbeats relative to said heartbeat. A fourth column of the real-time matrix is populated with an average of the square of the row of the normalized beat matrix corresponding to said heartbeat. A fifth column of the real-time matrix is populated with an average of the square of a derivative of the row of the normalized beat matrix corresponding to said heartbeat. A reference beat is determined by calculating an average between the rows of the normalized beat matrix having the relatively lowest ratio between the fourth column and fifth column values. A sixth column of the real-time matrix is populated with an average of the square of the reference beat. A seventh column of the real-time matrix is populated with an average of the square of the derivative of the reference beat. An eighth column of the real-time matrix is populated with a correlation coefficient between the reference beat and the row of the beat matrix corresponding to said heartbeat. A ninth column of the real-time matrix is populated with a correlation coefficient between the derivatives of the reference beat and the row of the beat matrix corresponding to said heartbeat. A tenth column of the real-time matrix is populated with a correlation coefficient between the squares of the reference beat and the row of the beat matrix corresponding to said heartbeat. An eleventh column of the real-time matrix is populated with a correlation coefficient between the squares of the derivatives of the reference beat and the row of the beat matrix corresponding to said heartbeat. The real-time matrix is transmitted to an at least one classifier in selective communication with the at least one computing device, thereby allowing the classifier to determine whether a given segment of the at least one ECG recording associated with the heart activity of the user contains arrhythmia-related heartbeats.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
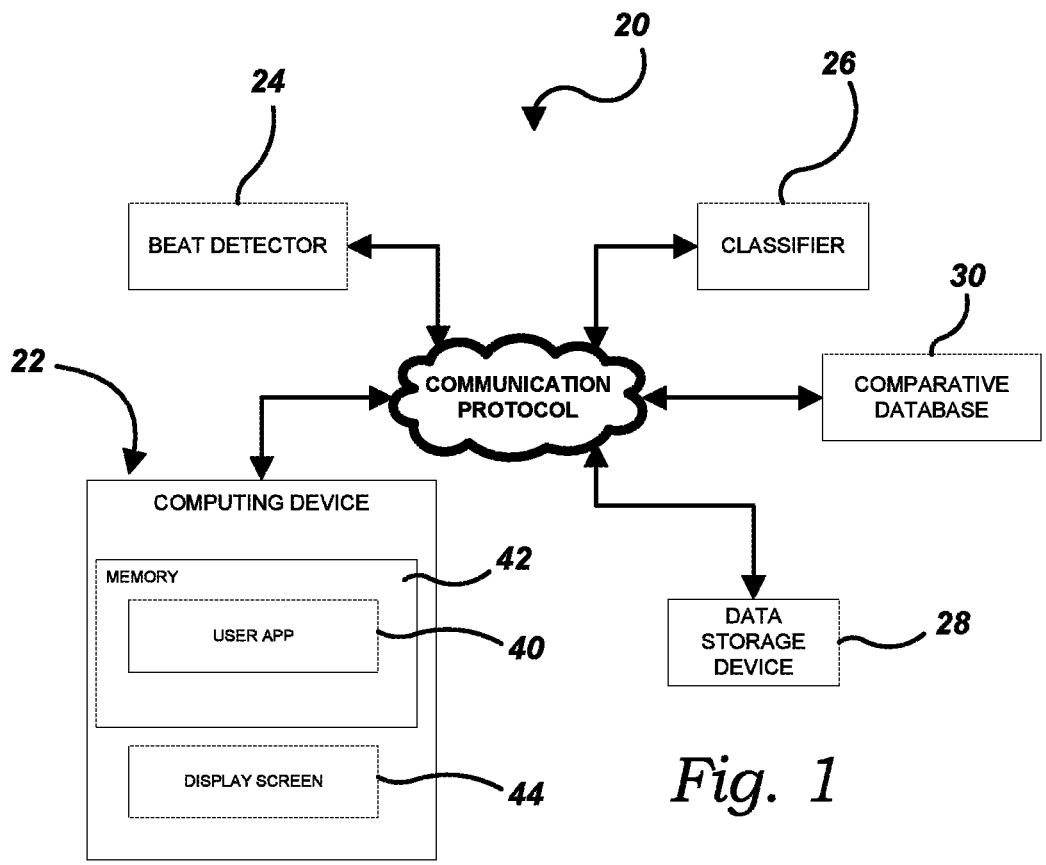
FIG. 1 is a simplified schematic view of an exemplary arrhythmia detection system, in accordance with at least one embodiment.
Figure 2:
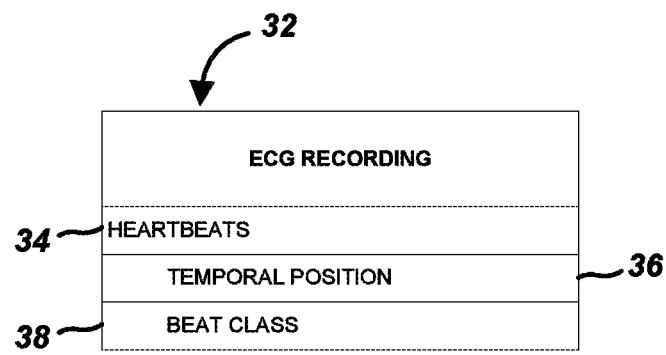
FIG. 2 is an architecture diagram of an exemplary ECG recording data structure, in accordance with at least one embodiment.

Turning now to FIG. 1, there is shown a simplified schematic view of an exemplary arrhythmia detection system 20. The system 20 provides, in at least one embodiment, an at least one computing device 22 configured for receiving and processing select data obtained by an at least one beat detector 24—such as an electrocardiogram ("ECG") device, for example (though any other type of device, sensor or combination thereof, now known or later developed, capable of substantially carrying out the functionality described herein may be substituted)—positioned and configured for obtaining biosignal data related to a user's heart activity (i.e., electrical activity of the user's heart). Accordingly, in at least one embodiment, the computing device 22 is in selective communication with the beat detector 24. In at least one embodiment, the computing device 22 and the beat detector 24 are one and the same—as such, it is intended that those terms as used herein are to be interchangeable with one another. Additionally, in at least one embodiment, an at least one classifier 26—such as an artificial neural network ("ANN"), for example (though any other type of device, system or combination thereof, now known or later developed, capable of substantially carrying out the functionality described herein may be substituted)—is in selective communication with the computing device 22 and configured for analyzing said data obtained by the at least one beat detector 24 and processed by the computing device 22, as discussed in detail below. In at least one embodiment, the computing device 22 and the classifier 26 are also one and the same—as such, it is intended that those terms as used herein are to be interchangeable with one another. Additionally, in at least one embodiment, an at least one data storage device 28 is in selective communication with the computing device 22 and configured for storing said data obtained by the beat detector 24, processed by the computing device 22, and analyzed by the classifier 26, along with certain other data as discussed further below. In at least one embodiment, the computing device 22 and data storage device 28 are also one and the same—as such, it is intended that those terms as used herein are to be interchangeable with one another.

In at least one embodiment, the computing device 22 (or, alternatively, the at least one classifier 26) is also in selective communication with an at least one comparative database 30 containing previously obtained biosignal data, the purpose of which is discussed further below. In at least one such embodiment, the at least one comparative database 30 is at least one of the MIT-BIH Arrhythmia Database ("MIT-AR"), the American Heart Association Database ("AHA"), and the MIT-BIH Supraventricular Arrhythmia Database ("MIT-SV"). However, in further embodiments, any other appropriate public or private comparative database 30, now known or later developed, may be substituted. In at least one such embodiment, and as discussed further below, the biosignal data contained in the at least one comparative database 30 includes a plurality of ECG recordings 32 representing a plurality of heartbeats 34 (i.e., the voltage versus time of a lead at a certain sampling rate), with each ECG recording 32 comprising a temporal position 36 of each of the heartbeats 34 in the ECG recording 32 along with annotation labels indicating a beat class 38 of each heartbeat 34. Accordingly, in at least one embodiment, each ECG recording 32 comprises two leads (i.e., two temporal time series of the voltage simultaneously measured along different directions)—one file indicating the temporal positions 36 of the detected beats in the voltage time series, and another file indicating the corresponding beat classes 38 of the detected beats 34. In at least one embodiment, the position of a given heartbeat 34 is determined using an automatic heartbeat detection algorithm, such as a real-time QRS detection algorithm for example. However, in further embodiments, any other means for detecting heartbeats 34, now known or later developed, may be substituted. As discussed further below, in at least one embodiment, the at least one comparative database 30 contains a discrete set k of ECG recordings 32—i.e., k=(1, 2, . . . , $nb_{ECG}$), where $nb_{ECG}$ is the number of ECG recordings 32 in the comparative database 30.

At the outset, it should be noted that communication between each of the at least one computing device 22, at least one beat detector 24, at least one classifier 26, at least one data storage device 28, and at least one comparative database 30 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the term "computing device" is intended to include any type of computing or electronic device, now known or later developed, capable of substantially carrying out the functionality described herein—such as desktop computers, mobile phones, smartphones, laptop computers, tablet computers, personal data assistants, gaming devices, wearable devices, etc. As such, the system 20 should not be read as being limited to use with any one particular type of computing or electronic device, even though certain exemplary devices may be mentioned or shown herein for illustrative purposes.

With continued reference to FIG. 1, in at least one embodiment, the at least one beat detector 24 is positioned on a wearable device, such as garment or other accessory being worn by the user, such as described in at least U.S. Patent Application Publication No. 2013/0338472, the contents of which are hereby incorporated herein by reference. In still further embodiments, the at least one beat detector 24 may be appropriately positioned in contact with (or proximal to) the user using any other means now known or later developed. Again, in further embodiments, the at least one beat detector 24 may be any other type of device, sensor or combination thereof, now known or later developed, capable of substantially carrying out the functionality described herein. In at least one embodiment, the computing device 22 is also removably engagable with the user—either directly with the user's body or with a wearable device, such as a garment or other accessory being worn by the user. In at least one such embodiment, the beat detector 24 is positioned within the computing device 22. In an alternate embodiment, the computing device 22 is positioned elsewhere—either still local to the user or remotely, or even divided, with some of the functional units implemented in a computing device 22 local to the user and other units implemented in remote computer work stations.

In at least one embodiment, the computing device 22 contains the hardware and software necessary to carry out the exemplary methods for classifying arrhythmia-related heartbeats 34, as described herein. Furthermore, in at least one embodiment, the computing device 22 comprises a plurality of computing devices selectively working in concert with one another to carry out the exemplary methods for classifying arrhythmia-related heartbeats 34, as described herein. In at least one embodiment, the computing device 22 provides a user application 40 residing locally in memory 42 on the computing device 22, the user application 40 being configured for selectively communicating with each of the at least one beat detector 24, classifier 26 and comparative database 30, as discussed further below. It should be noted that the term "memory" is intended to include any type of electronic storage medium (or combination of storage mediums) now known or later developed, such as local hard drives, RAM, flash memory, secure digital ("SD") cards, external storage devices, network or cloud storage devices, integrated circuits, etc. In at least one embodiment, the computing device 22 provides an at least one display screen 44 configured for displaying the classification data, as discussed in detail below.

In use, in at least one embodiment, the system 20 is capable of classifying arrhythmia-related heartbeats 34 based on extracted data from an at least one lead of an ECG recording 32. In at least one embodiment, as illustrated in the flow diagram of FIG. 3, the at least one classifier 26 is first trained appropriately. In at least one such embodiment, the user application 40 of the computing device 22 accesses a first of the at least one comparative database 30 (302), and moves to a first ECG recording 32 of the set k in the at least one comparative database 30 (304), and resamples the ECG recording 32 to an appropriate, common sampling rate (306). In at least one embodiment, the common sampling rate is 250 Hz. However, in further embodiments, the common sampling rate may be any other sampling rate now known or later determined. In at least one embodiment, the ECG recording 32 is resampled by interpolating the ECG recording 32 to the common sampling rate. It should be noted that where the original sampling rate of the ECG recording 32 is already that of the common sampling rate, this particular step may be skipped. In at least one embodiment, if the temporal positions 36 of the heartbeats 34 associated with the ECG recording 32 is in sampled units, the temporal positions 36 are converted to time units (308).

Additionally, in at least one embodiment, each of the associated beat classes 38 is converted to a binary value (310). In at least one such embodiment, all heartbeats 34 with a supraventricular origin ("SVE"—corresponding to the types of non-ectopic and supraventricular ectopic beats of the ANSI/AAMI EC57:1998 standard—) are assigned a binary value of "0," and all heartbeats 34 with a ventricular origin ("VE"—corresponding to the types of ventricular and fusion ectopic beats of the ANSI/AAMI EC57:1998 standard) are assigned a binary value of "1". It should be noted that while the system 20 is described herein as being configured for analyzing and classifying ventricular ectopic heartbeats 34 for illustrative purposes, in further embodiments, the system 20 may be configured for analyzing and classifying any other type of arrhythmia-related heartbeats 34 based on extracted data from an at least one lead of an ECG recording 32 using the methods described herein. Thus, the present invention should not be read as being limited to only ventricular ectopic heartbeats 34.

Figure 3:
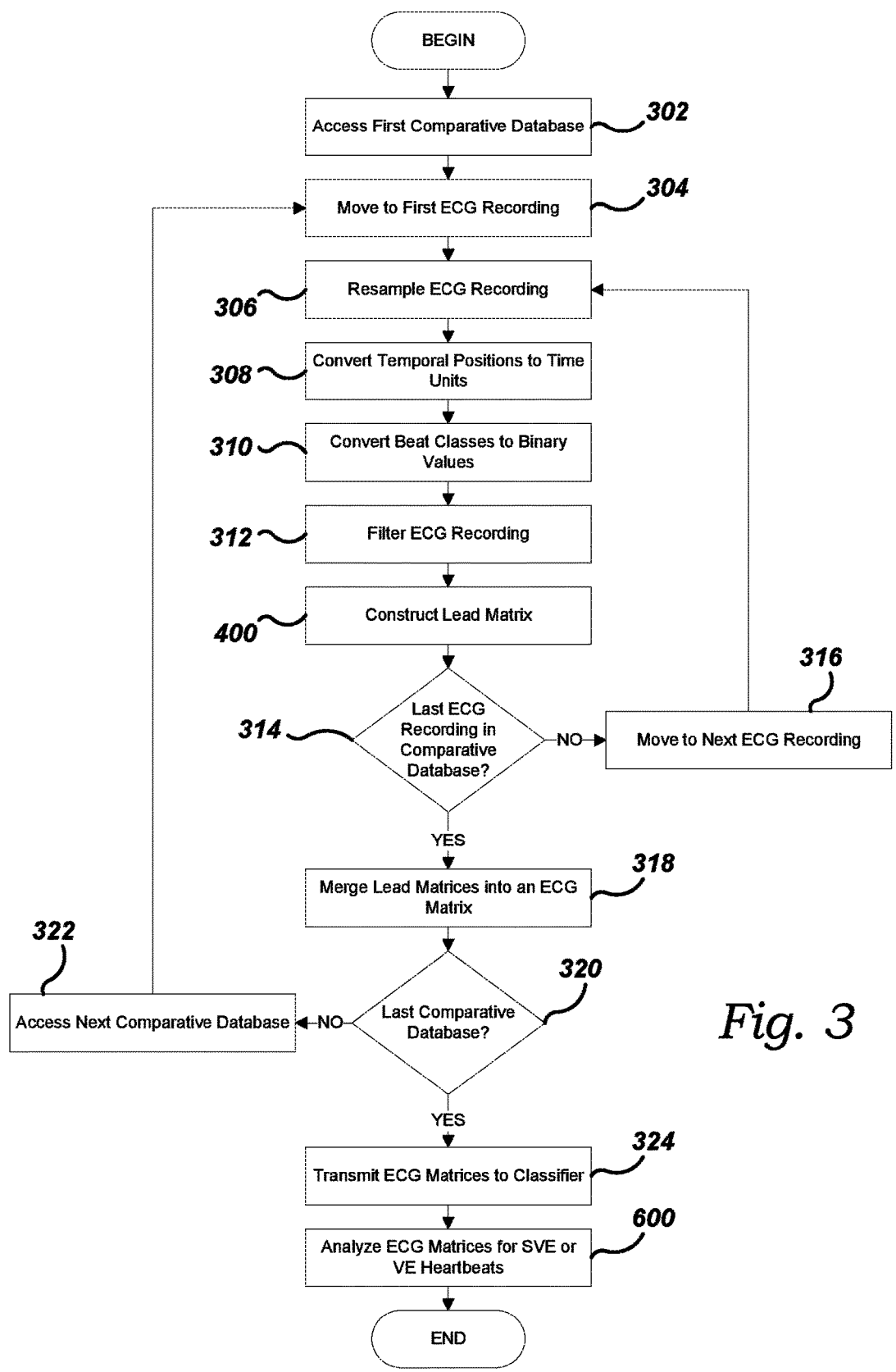
FIG. 3 is a flow diagram of an exemplary method for training an at least one classifier, in accordance with at least one embodiment.

With continued referenced to FIG. 3, in at least one embodiment, the ECG recording 32 is filtered to remove any unwanted high frequency noise and to correct the baseline (312). In at least one such embodiment, the user application 40 utilizes a second order Butterworth high-pass filter with a cutoff frequency of 0.5 Hz and a finite impulse response filter of 12th order with 35 Hz at 3 decibels. However, in further embodiments, any other means and/or methods, now known or later developed, for removing unwanted high frequency noise and correcting the baseline of the ECG recording 32, may be substituted. In at least one embodiment, the temporal position 36 of each heartbeat 34 is adjusted to be at the largest local extrema in the QRS complex of said heartbeat 34. The adjusted heartbeats 34 correspond to the position of the maximum peak of the squared temporal waveform within a small window around the original position (though, in further embodiments, any other point can be chosen).

Figure 4:
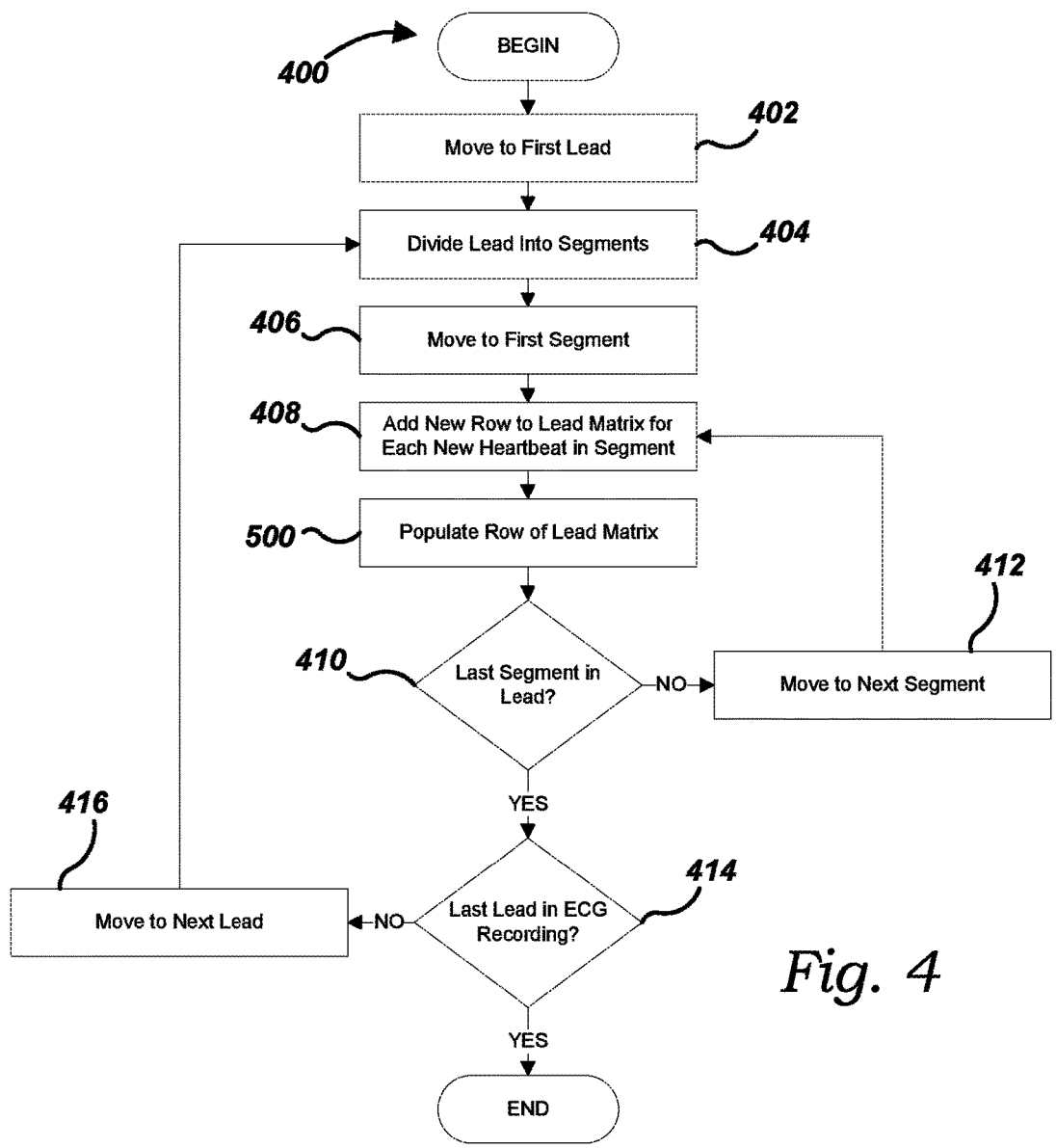
FIG. 4 is a flow diagram of an exemplary method for constructing an exemplary lead matrix representing an at least one ECG recording, in accordance with at least one embodiment.

With continued reference to FIG. 3, in at least one embodiment, the user application 40 next constructs a lead matrix for each of the at least one lead of the ECG recording 32 (400). In at least one embodiment, each of the at least one ECG recording 32 contains a discrete set j of leads—i.e., j=(1, 2, . . . , $nb_{lead}$), where $nb_{lead}$ is the number of leads in the associated ECG recording 32. In a bit more detail, in at least one such embodiment, the lead matrix is constructed using the formula $Data_{lead(j)}^{ECG(k)}$=[number of beats of the ECG(k)×features], where each column (i.e., feature) represents a characteristic that could be used by the user application 40 to better distinguish between a SVE or VE heartbeat 34. In at least one embodiment, the lead matrix is constructed in sequential steps. In a bit more detail, as illustrated in the flow diagram of FIG. 4, in at least one such embodiment, the user application 40 of the computing device 22 moves to a first lead j in the current ECG recording 32 (402), and the lead is divided into a plurality of non-overlapping segments p of a pre-determined temporal length or duration (404), such as ten minutes or 500 heartbeats for example (though, in further embodiments, any other pre-determined temporal length may be substituted). In at least one alternate embodiment, the lead is divided into a plurality of overlapping segments p of a pre-determined temporal length or duration, such as ten minutes or 500 heartbeats for example, with each segment p being captured at a pre-determined frequency, such as every T seconds (for example T=10) or H heartbeats (for example H=10). In other words, in such an embodiment, the segment p is a sliding window of a pre-determined temporal length or duration. As discussed in detail below, the features of the heartbeats 34 of each lead are then calculated consecutively—i.e., $\text{Data}_{lead(j)}^{ECG(k)}=[D_1, D_2, \ldots, D_M]$. Accordingly, $D_p$ with $p=1, \ldots, M$ contains only the features of the new heartbeats 34 within the p segments of pre-determined temporal length in which the ECG lead has been divided, with its size being [number of the new heartbeats 34 of the lead in the p segment×features]. Thus, for example, if the p are non-overlapping segments, $D_p$=[number of the heartbeats 34 of the lead in the p segment×features]. In at least one alternate embodiment utilizing p overlapping segments, $D_p$=[last H heartbeats 34 in the p segment×features], i.e., as the p segment is now defined with a slide window, only the features for the last H heartbeats are calculated. In at least one embodiment, when using non-overlapping segments, each row of the lead matrix corresponds to a successive heartbeat 34 i of the associated lead. In other words, in such an embodiment, each row of the lead matrix represents one heartbeat 34 of the associated lead. Thus, as illustrated in the flow diagram of FIG. 4, in at least one embodiment, the user application 40 moves to a first segment p in the current lead (406), and for each heartbeat 34 of the associated segment, the user application 40 adds a new row to the lead matrix corresponding to said heartbeat 34 (408). As illustrated in the flow diagram of FIG. 5, for each of the at least one heartbeat 34 in the segment, a first column of the lead matrix is populated with an interbeat interval ("RR") between the current heartbeat 34 and the immediately preceding heartbeat 34 (502). The interbeat interval is the time interval between successive heartbeats 34 within the lead, where RR(i) corresponds to the time difference between a given heartbeat 34 i and an immediately preceding heartbeat 34 (i-1). In at least one embodiment, given that the interbeat intervals are calculated from relative temporal positions 36 of the heartbeats 34, the RR of a first heartbeat 34 in the lead is set to zero. In at least one further embodiment, the feature-related interbeat intervals are calculated based on one or more of a pre RR, a post RR, an RR past average—i.e., mean(RR(1:-1:segment))—or a standard deviation of successive differences between adjacent RR values—i.e., pre RR-post RR. A second column of the lead matrix is populated with the interbeat interval between the current heartbeat 34 and the immediately succeeding heartbeat 34 (504). In at least one such embodiment, the second column value for the last heartbeat 34 in the lead is set to zero. A third column of the lead matrix is populated with an interval mean calculated over a pre-determined number of preceding heartbeats 34 in the lead, relative to the current heartbeat 34 (506), such as five hundred preceding heartbeats 34 for example (though, in further embodiments, any other pre-determined number of preceding and succeeding heartbeats 34 may be substituted). In at least one such embodiment, for the first five hundred heartbeats 34 of the lead, the interval mean only takes into account the available interbeat intervals.

Figure 5:
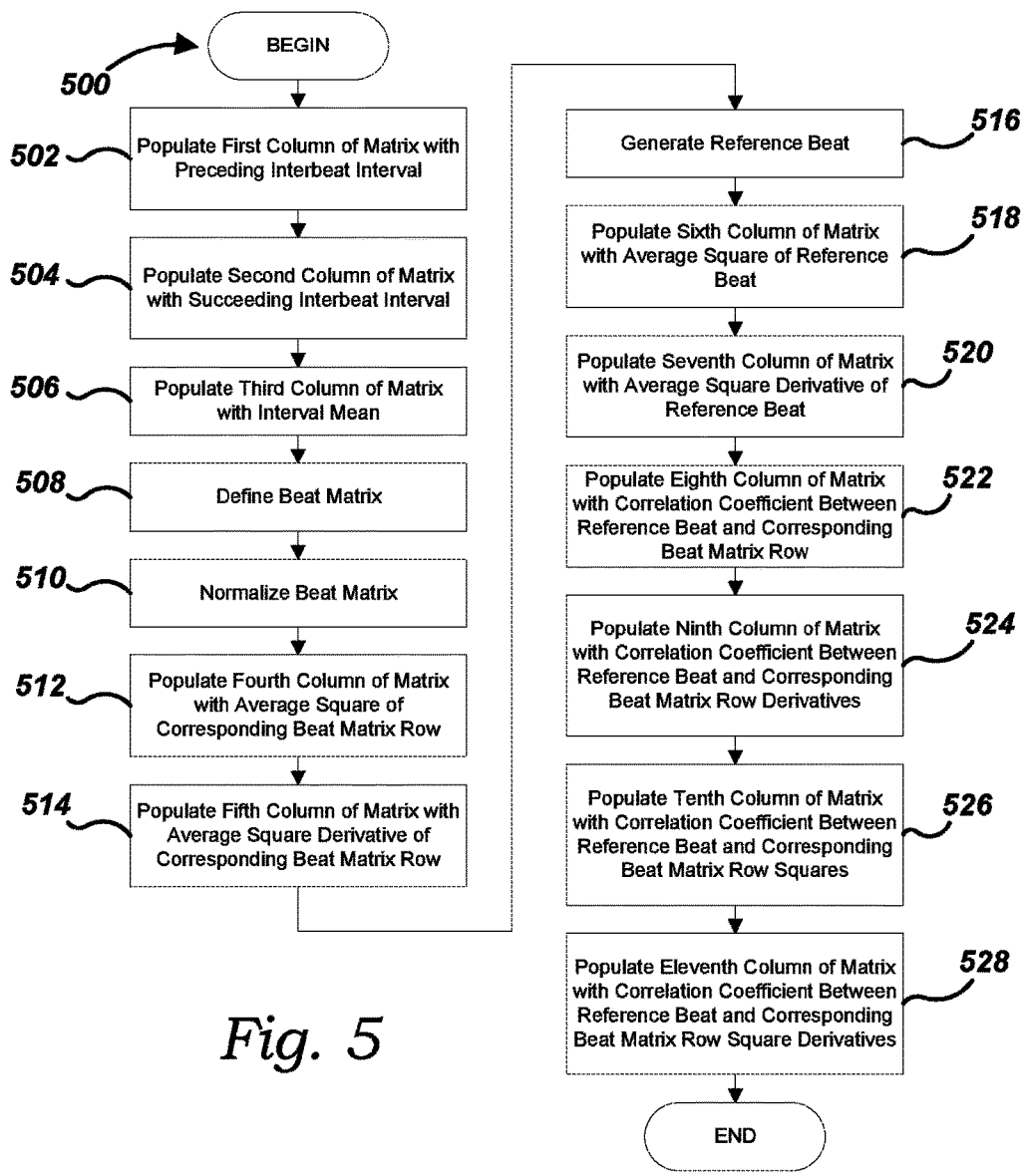
FIG. 5 is a flow diagram of an exemplary method for constructing either an exemplary lead matrix or an exemplary real-time matrix, in accordance with at least one embodiment.

With continued reference to FIG. 5, in at least one embodiment, the user application 40 defines a beat matrix (508), with each row of the beat matrix corresponding to a successive heartbeat 34 in the associated segment p, within a window of pre-determined temporal length (such as 520 milliseconds for example) around the temporal position 36 of each heartbeat 34. In a bit more detail, in at least one such embodiment, the beat matrix is defined using the formula Beat=[$\text{nb}_{Beats}(p) \times \text{nb}_{samples}$], where $\text{nb}_{Beats}(p)$ is the number of detected heartbeats 34 in the segment p and $\text{nb}_{samples}$ is the number of samples taken by the user application 40 around the position of a given heartbeat 34. In at least one embodiment, the number of samples taken is 130, with 50 samples immediately preceding the reference point of the heartbeat 34 and 80 samples immediately after the reference point of the heartbeat 34. However, in further embodiments, any other number of samples may be substituted. Once the beat matrix has been defined, the beat matrix is normalized ("$\text{Beat}_{norm}$") such that all rows of the beat matrix are normalized to have a mean of zero and a standard deviation of one (510). From there, in at least one embodiment, a fourth column of the lead matrix is populated with an average of the square of the corresponding row of the normalized beat matrix (512)—i.e., an estimation of the area of the heartbeat 34 within the 520-millisecond window—using the formula mean($\text{Beat}_{norm}(i, :)^2$). Additionally, a fifth column of the lead matrix is populated with an average of the square of a derivative of the corresponding row of the normalized beat matrix (514)—i.e., a rough estimation of the rate of change—using the formula mean(($\text{Beat}'_{norm}(i, :))^2$).

With continued reference to FIG. 5, in at least one embodiment, the user application 40 generates a reference beat (516) by calculating an average between the rows of the normalized beat matrix having the relatively lowest ratio between the fourth column and fifth column values. A sixth column of the lead matrix is then populated with an average of the square of the reference beat over a window of pre-determined temporal length (518), such as 520 milliseconds for example, using the formula mean($\text{Ref}^2$). Additionally, a seventh column of the lead matrix is populated with an average of the square of the derivative of the reference beat over a window of a pre-determined temporal length (520), such as 520 milliseconds for example, using the formula mean(($\text{Ref}')^2$).

With continued referenced to FIG. 5, in at least one embodiment, the user application 40 populates each of an eighth column, ninth column, tenth column and eleventh column of the lead matrix using the following correlation coefficient formula:

$$C(X, Y) = \frac{\sum_{i=1}^{n}(X_i - \overline{X})(Y_i - \overline{Y})}{\sqrt{\sum_{i=1}^{n}(X_i - \overline{X})^2 \sum_{i=1}^{n}(Y_i - \overline{Y})^2}}$$

where the summation runs over a window of 520 milliseconds (i.e., 130 samples, with 50 samples before and 80 samples after a given heartbeat 34). In at least one embodiment, the eighth column is populated with a correlation coefficient between the reference beat and the corresponding row of the beat matrix (522)—i.e., C(Ref,Beat(i)). The ninth column is populated with a correlation coefficient between the derivatives of the reference beat and the corresponding row of the beat matrix (524)—i.e., C(Ref,Beat(i)'). The tenth column is populated with a correlation coefficient between the squares of the reference beat and the corresponding row of the beat matrix (526)—i.e., C($\text{Ref}^2$, $\text{Beat}(i)^2$). The eleventh column is populated with a correlation coefficient between the squares of the derivatives of the reference beat and the corresponding row of the beat matrix (528)—i.e., C($(\text{Ref}')^2$, $(\text{Beat}(i)')^2$). It should be noted that, in at least one embodiment, the above described columns may be arranged in any other order now known or later conceived. Additionally, in at least one embodiment, one or more of the above described columns may be omitted from the lead matrix or columns with other indicators can be added. Thus, the above-described structure of the lead matrix is merely exemplary.

Referring again to FIG. 4, in at least one embodiment, the user application 40 moves to the next segment p in the current lead (412) and repeats steps 408 and 500. This process is repeated until all segments p in the current lead have been processed (410), at which point the user application 40 moves to the next lead j in the ECG recording 32 (416) and repeats steps 404 through 412. This process is repeated until all leads j in the current ECG recording 32 have been processed (414).

Referring again to FIG. 3, in at least one embodiment, the user application 40 moves to the next ECG recording 32 of the set k in the at least one comparative database 30 (316) and repeats steps 306 through 400. This process repeats until all ECG recordings 32 in the at least one comparative database 30 have been processed (314). In at least one embodiment, the user application 40 has now generated $[nb_{ECG} \times nb_{lead}]$ lead matrices; one per each ECG recording 32 k and the corresponding at least one lead j. In at least one embodiment, the user application 40 merges the at least one lead matrix associated with a given ECG recording 32 (318)—i.e., $Data_{lead(j)}^{ECG(k)}$—into a single ECG matrix per lead, such that each ECG recording 32 is then represented by a corresponding single ECG matrix per lead—i.e., $DATA_{database}^{j} = [DATA_{lead(j)}^{ECG(1)}, DATA_{lead(j)}^{ECG(2)}, \ldots, DATA_{lead(j)}^{ECG(nb_{ECG})}]$, where $j=1, \ldots, nb_{lead}$, and $nb_{lead}$ is the number of leads in the associated ECG recording 32.

With continued reference to FIG. 3, in at least one embodiment, the user application 40 moves to the next comparative database 30 (322) and repeats steps 304 through 318. This process repeats until all comparative databases 30 have been processed (320). In at least one embodiment, each heartbeat 34 is represented as a d-dimensional vector—i.e., d predictors or features/columns)—organized in the ECG matrix according to the associated comparative database 30 and lead of the heartbeat 34. In at least one embodiment, the size of each ECG matrix is [number of beats of the comparative database×11]. The at least one ECG matrix is then transmitted to the at least one classifier 26 (324) together with the appropriate label for each beat (i.e., 0 and 1—for the SVE and VE classes, respectively) which, in turn, uses the at least one vector matrix to train itself to be able to determine whether a future heartbeat 34 of a single lead of an ECG recording 32 contains supraventricular ectopic ("SVE") or ventricular ectopic ("VE") heartbeats 34 (600). In at least one embodiment, this training procedure (i.e., steps 302 through 322) is performed only once in the lifetime of a given classifier 26, and use of the at least one comparative database 30 is only needed for the training procedure.

Figure 6:
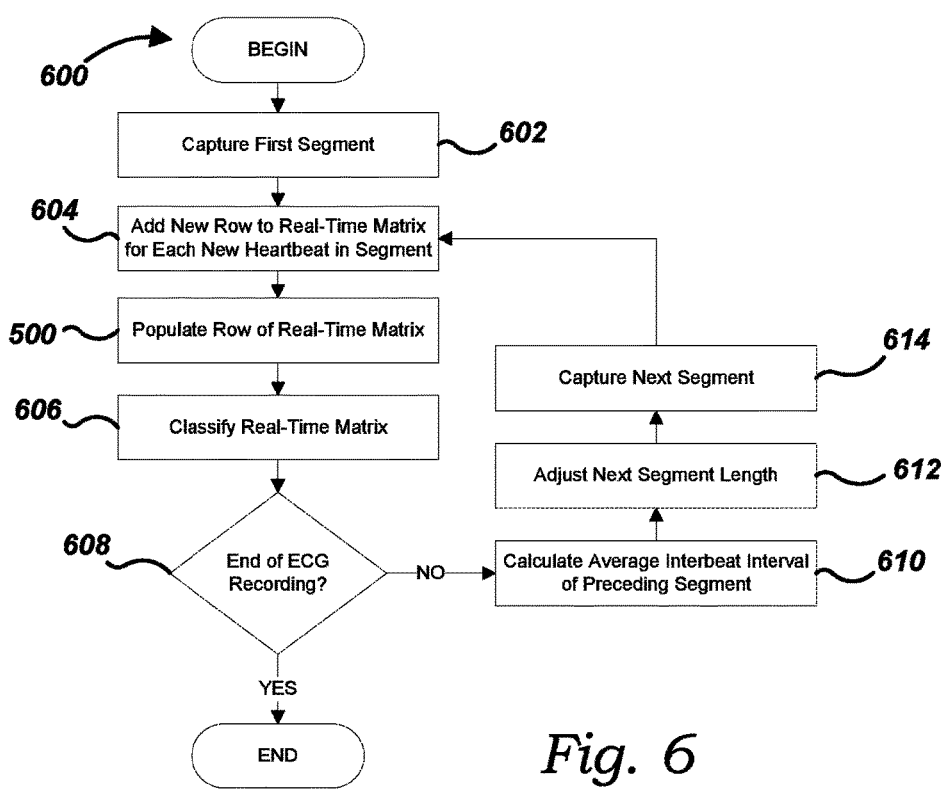
FIG. 6 is a flow diagram of an exemplary method for analyzing and classifying arrhythmia-related heartbeats of a user, in accordance with at least one embodiment.

In at least one embodiment, as illustrated in FIG. 6, the user application 40 analyzes a given segment of a single lead of an ECG recording 32 using a method similar to that used for constructing the lead matrix described above. In a bit more detail, in at least one embodiment, for a given lead of an ECG recording 32, a real-time matrix $D_p$ is constructed, with $p=1, \ldots, M$ containing only the features of the heartbeats 34 within the p segments of pre-determined temporal length in which the ECG lead has been divided, with its size being [number of heartbeats 34 of the lead in the p segment×features]. The user application 40 captures the first segment (602), and for each heartbeat 34 of the associated segment, the user application 40 adds a new row to the real-time matrix corresponding to said heartbeat 34 (604).

For each of the at least one heartbeat 34 in the segment, the columns of the real-time matrix are populated (500) as described above in steps 502 through 528. The real-time matrix is then transmitted to the trained at least one classifier 26 which, in turn, analyzes the real-time matrix to determine whether it contains supraventricular ectopic ("SVE") or ventricular ectopic ("VE") heartbeats 34 (606). In at least one embodiment, before capturing a further segment of the ECG recording 32, the user application 40 calculates an average of the interbeat interval values of the preceding segment (610), then adjusts the length of the further segment (i.e., the heartbeat window) to be a pre-determined percentage of the calculated preceding interbeat interval average (612), which allows the user application 40 to dynamically adjust the size/length of each segment based on this general method. The further segment is then captured (614) and steps 604 through 606 are repeated. This process is repeated until all segments p in the lead have been processed (608).

In at least one embodiment, the at least one classifier 26 utilizes a reservoir computing technique—specifically, Echo State Networks ("ESN"). In a bit more detail, ESN is an architecture for recurrent neural networks where the input weights and connection weights between the internal nodes—usually called "neurons"—are randomly generated and kept fixed. Only the output weights are optimized using (usually) a simple linear regression. ESN is a recurrent discrete-time neural network with d input nodes, where d is the dimensionality of the input space, N internal (reservoir) nodes, and/output nodes. The connections between the input nodes and the internal nodes are given by a N×d input weight matrix $W^{in}$. The connections among the internal nodes are defined by an N×N matrix, W, and connections from internal nodes to output nodes are given in a N×I weight output matrix $W^{out}$. The matrix $W^{in}$ and W are random and usually drawn from a uniform distribution over [−1, 1]. The only weights to be trained in this approach are those corresponding to the reservoir-output connections, $W^{out}$. The state of all internal nodes, r(n), is updated at each time step (n) (this mean each beat) according to the formula $r(n)=F(\gamma W^{in} \times (n) + \beta W r(n-1))$, where F is the ESN activation function, x(n) is the input (i.e. a row of the real time or lead matrix), γ is an input scaling parameter and β is the connection scaling factor. In at least one embodiment, the sigmoid function is used as the activation function. In at least one further embodiment, other activation functions such as rectifiers can be used.

In at least one embodiment, the response of the ESN to the input, r(n), is used to calculate the expected outputs, o(n), according to the formula $o(n)=W^{out} r(n)$, where $W^{out}$ are the output weights of ESN. In at least one embodiment, the output weights are computed by a linear regression method during the training procedure. In at least one such embodiment, an ESN with ring topology is used—i.e., the internal nodes are organized in a circle. In such an embodiment, the connection matrix is no longer a random matrix and has only non-zero elements in the lower sub-diagonal $W_{i+1,i}=1$ and at the upper-right corner $W_{1,N}=1$, where N is the number of nodes in the network. The input dimensionality and therefore the number of input nodes is d=11 (number of features). The number of output nodes is I=1, as the output is a binary scalar (0 or 1 in this embodiment). In at least one embodiment, the classifier 26 deals with a classification task that requires a binary output—i.e., 0 and 1—for the SVE' and VE classes, respectively. Thus, the continuous output given by the expected output formula must be converted into a binary one by means of a decision threshold. Standard classification algorithms generally use a default decision threshold of 0.5.

In at least one embodiment, the typical model construction decisions in a ring ESN include: setting the network size (N), the input connection matrix $W^{in}$ and the scaling parameters $\gamma$ and $\beta$. These parameters, together with the output weights, are varied while training the at least one classifier 26. In a bit more detail, in at least one embodiment, the system utilizes the heartbeats 34 from the at least one comparative database 30 to train the ESN. Heartbeats 34 from the same ECG recording 32, but different leads, are treated as independent heartbeats 34 to increase the number of training samples. The input is fed into the ESN in a sequential manner—i.e., one row of the matrix $DATA_{database}^{j}$ at a time. In at least one embodiment, to set the network size (N) and the scaling parameters $\gamma$ and $\beta$, the heartbeats 34 of the at least one comparative database 30 are used for training. Optimizing N, $\gamma$ and $\beta$ at the same time can be very time-consuming and inefficient. Thus, in at least one embodiment, the classifier first fixes the number of internal units N to a typical value (such as 400, for example) and training ESNs with the heartbeats 34 of the at least one comparative database 30 for $\gamma=\alpha/\sqrt{d}$, with $\alpha$ changing from 0.1 to 2 in steps of 0.25 and $\beta$ changing from 0.1 to 1 in steps of 0.1. In at least one embodiment, to avoid an undesired dependence on the sparsity of the input connections, the classifier averages over ten different input random matrices $W^{in}$. Thus, the training is repeated ten times with different $W^{in}$. The classifier then takes the combination of ($\beta$ & $\gamma$) that gives the best average result over the ten realizations on a validation set of the at least one comparative database 30. After that, the same procedure is used to find the optimal reservoir size N for these $\beta$ and $\gamma$ values. In at least one embodiment, for the classification between SVE' and VE heartbeats 34, the parameter values are N=200 (the number of nodes), $\gamma=1/\sqrt{d}$ and $\beta=0.6$. It should be noted that d is the input dimension—i.e., the number of features used per heartbeat 34, such as 11 for example. In at least one embodiment, the optimum output connections are then determined. The ESN is trained with these parameters to obtain the weights $W^{out}$ by a simple linear regression. This process is repeated ten times, each repetition with a new randomly generated input matrix $W^{in}$. Thus, in at least one embodiment, the at least one classifier 26 is able to distinguish between SVE' and VE heartbeats 34 using the information contained in at least one segment of a single lead of an ECG recording 32.

Aspects of the present specification may also be described as follows:

1. A method for analyzing and classifying arrhythmia-related heartbeats of a user based on an at least one biosignal associated with heart activity of the user as captured by an at least one lead of an at least one ECG recording, the method comprising the steps of: implementing a user application residing in memory on an at least one computing device, the at least one computing device in selective communication with an at least one comparative database containing an at least one ECG recording representing a plurality of heartbeats, each said ECG recording comprising a temporal position and a beat class associated with each represented heartbeat; constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat; dividing said at least one lead into a plurality of segments of a pre-determined temporal length; for each of the at least one segment: defining a beat matrix, each of an at least one row of said beat matrix representing a successive at least one heartbeat of said segment, and each of an at least one column of said beat matrix representing an at least one sample of said ECG recording taken around the temporal position of said at least one heartbeat; normalizing the beat matrix such that all rows of said beat matrix have a mean of zero and a standard deviation of one; and for each of the at least one heartbeat within said segment: adding a row for said heartbeat to the real-time matrix; populating a first column of the real-time matrix with an interbeat interval between said heartbeat and an immediately preceding heartbeat; populating a second column of the real-time matrix with an interbeat interval between said heartbeat and an immediately succeeding heartbeat; populating a third column of the real-time matrix with an interval mean calculated over a pre-determined number of preceding and succeeding heartbeats relative to said heartbeat; populating a fourth column of the real-time matrix with an average of the square of the row of the normalized beat matrix corresponding to said heartbeat; populating a fifth column of the real-time matrix with an average of the square of a derivative of the row of the normalized beat matrix corresponding to said heartbeat; determining a reference beat by calculating an average between the rows of the beat matrix having the relatively lowest ratio between the fourth column and fifth column values; populating a sixth column of the real-time matrix with an average of the square of the reference beat; populating a seventh column of the real-time matrix with an average of the square of the derivative of the reference beat; populating an eighth column of the real-time matrix with a correlation coefficient between the reference beat and the row of the beat matrix corresponding to said heartbeat; populating a ninth column of the real-time matrix with a correlation coefficient between the derivatives of the reference beat and the row of the beat matrix corresponding to said heartbeat; populating a tenth column of the real-time matrix with a correlation coefficient between the squares of the reference beat and the row of the beat matrix corresponding to said heartbeat; and populating an eleventh column of the real-time matrix with a correlation coefficient between the squares of the derivatives of the reference beat and the row of the beat matrix corresponding to said heartbeat; transmitting the real-time matrix to an at least one classifier in selective communication with the at least one computing device; and determining whether said segment contains arrhythmia-related heartbeats.

2. The method according to embodiment 1, wherein the step of dividing said lead into a plurality of segments further comprises the step of dividing said lead into a plurality of non-overlapping segments of a pre-determined temporal length.

3. The method according to embodiments 1-2, wherein the step of dividing said lead into a plurality of non-overlapping segments of a pre-determined temporal length, further comprises the step of dividing said lead into a plurality of non-overlapping segments having a temporal length of ten minutes each.

4. The method according to embodiments 1-3, wherein the step of dividing said lead into a plurality of segments further comprises the step of dividing said lead into a plurality of overlapping segments of a pre-determined temporal length, with each segment being captured at a pre-determined frequency.

5. The method according to embodiments 1-4, wherein the step of dividing said lead into a plurality of overlapping segments of a pre-determined temporal length, further comprises the step of dividing said lead into a plurality of overlapping segments having a temporal length of ten minutes each.

6. The method according to embodiments 1-5, wherein the step of dividing said lead into a plurality of segments further comprises the steps of, for each of the at least one segment: calculating an average of the at least one interbeat interval value of a given segment; and adjusting the length of an immediately succeeding segment to equal a pre-determined percentage of the calculated interbeat interval average of said given segment.

7. The method according to embodiments 1-6, further comprising the step of training the at least one classifier.

8. The method according to embodiments 1-7, further comprising the steps of, for each of the at least one comparative database: for each of the at least one ECG recording contained in said comparative database: for each of the at least one lead of said ECG recording: defining a lead matrix, each of an at least one row of said lead matrix representing a successive at least one heartbeat of said ECG recording, and each of an at least one column of said lead matrix representing a characteristic of said at least one heartbeat; dividing said lead into a plurality of segments of a pre-determined temporal length; and for each of the at least one segment: defining a beat matrix, each of an at least one row of said beat matrix representing a successive at least one heartbeat of said segment, and each of an at least one column of said beat matrix representing an at least one sample of said ECG recording taken around the temporal position of said at least one heartbeat; normalizing the beat matrix such that all rows of said beat matrix have a mean of zero and a standard deviation of one; and for each of the at least one heartbeat within said segment: adding a row for said heartbeat to the lead matrix; populating a first column of the lead matrix with an interbeat interval between said heartbeat and an immediately preceding heartbeat; populating a second column of the lead matrix with an interbeat interval between said heartbeat and an immediately succeeding heartbeat; populating a third column of the lead matrix with an interval mean calculated over a pre-determined number of preceding and succeeding heartbeats relative to said heartbeat; populating a fourth column of the lead matrix with an average of the square of the row of the normalized beat matrix corresponding to said heartbeat; populating a fifth column of the lead matrix with an average of the square of a derivative of the row of the normalized beat matrix corresponding to said heartbeat; determining a reference beat by calculating an average between the rows of the beat matrix having the relatively lowest ratio between the fourth column and fifth column values; populating a sixth column of the lead matrix with an average of the square of the reference beat; populating a seventh column of the lead matrix with an average of the square of the derivative of the reference beat; populating an eighth column of the lead matrix with a correlation coefficient between the reference beat and the row of the beat matrix corresponding to said heartbeat; populating a ninth column of the lead matrix with a correlation coefficient between the derivatives of the reference beat and the row of the beat matrix corresponding to said heartbeat; populating a tenth column of the lead matrix with a correlation coefficient between the squares of the reference beat and the row of the beat matrix corresponding to said heartbeat; and populating an eleventh column of the lead matrix with a correlation coefficient between the squares of the derivatives of the reference beat and the row of the beat matrix corresponding to said heartbeat; and merging each of the at least one lead matrix into a single ECG matrix associated with the at least one ECG recording contained in said comparative database.

9. The method according to embodiments 1-8, further comprising the steps of, for each of the at least one ECG recording contained in said comparative database: resampling said ECG recording to an appropriate common sampling rate; converting the temporal position associated with each represented heartbeat of said ECG recording to time units; and converting the beat class associated with each represented heartbeat of said ECG recording to a binary value.

10. The method according to embodiments 1-9, wherein the step of resampling said ECG recording to an appropriate common sampling rate, further comprises the step of resampling said ECG recording to 250 Hz.

11. The method according to embodiments 1-10, wherein the step of converting the beat class associated with each represented heartbeat of said ECG recording to a binary value, further comprises the steps of: upon determining that a given heartbeat has a supraventricular origin, assigning the beat class for said heartbeat a binary value of zero; and upon determining that a given heartbeat has a ventricular origin, assigning the beat class for said heartbeat a binary value of one.

12. The method according to embodiments 1-11, further comprising the step of, for each of the at least one ECG recording contained in said comparative database, filtering said ECG recording to remove any unwanted high frequency noise and to correct a baseline of said ECG recording.

13. The method according to embodiments 1-12, wherein the step of filtering said ECG recording further comprises the step of filtering said ECG recording using a second order Butterworth high-pass filter with a cutoff frequency of 0.5 Hz and a finite impulse response filter of 12th order with 35 Hz at 3 decibels.

14. The method according to embodiments 1-13, further comprising the step of, for each of the at least one ECG recording contained in said comparative database, adjusting the temporal position associated with each represented heartbeat of said ECG recording to be at the largest local extrema in a QRS complex of said heartbeat.

15. The method according to embodiments 1-14, wherein the step of populating the third column of the real-time matrix, further comprising the step of populating the third column with an interval mean calculated over ten preceding heartbeats and ten succeeding heartbeats relative to said heartbeat.

16. The method according to embodiments 1-15, wherein the step of populating the third column of the lead matrix, further comprising the step of populating the third column with an interval mean calculated over ten preceding heartbeats and ten succeeding heartbeats relative to said heartbeat.

17. The method according to embodiments 1-16, wherein the step of defining the beat matrix further comprises the step of populating the columns of the beat matrix with at least one sample of said ECG recording taken within a window of 520 milliseconds around the temporal position of said at least one heartbeat.

18. The method according to embodiments 1-17, wherein the step of defining the beat matrix further comprises the step of populating the columns of the beat matrix with thirty samples of said ECG recording taken before the temporal position of said at least one heartbeat, and sixty samples of said ECG recording taken after the temporal position of said at least one heartbeat.

19. The method according to embodiments 1-18, wherein the step of populating the sixth column of the real-time matrix further comprises the step of populating the sixth column with an average of the square of the reference beat over a window of 520 milliseconds.

20. The method according to embodiments 1-19, wherein the step of populating the sixth column of the lead matrix further comprises the step of populating the sixth column with an average of the square of the reference beat over a window of 520 milliseconds.

21. The method according to embodiments 1-20, wherein the step of populating the seventh column of the real-time matrix further comprises the step of populating the seventh column with an average of the square of the derivative of the reference beat over a window of 520 milliseconds.

22. The method according to embodiments 1-21, wherein the step of populating the seventh column of the lead matrix further comprises the step of populating the seventh column with an average of the square of the derivative of the reference beat over a window of 520 milliseconds.

23. A method for analyzing and classifying arrhythmia-related heartbeats of a user based on an at least one biosignal associated with heart activity of the user as captured by an at least one lead of an at least one ECG recording, the method comprising the steps of: implementing a user application residing in memory on an at least one computing device, the at least one computing device in selective communication with an at least one comparative database containing an at least one ECG recording representing a plurality of heartbeats, each said ECG recording comprising a temporal position and a beat class associated with each represented heartbeat; constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat; dividing said at least one lead into a plurality of segments of a pre-determined temporal length; for each of the at least one segment: defining a beat matrix, each of an at least one row of said beat matrix representing a successive at least one heartbeat of said segment, and each of an at least one column of said beat matrix representing an at least one sample of said ECG recording taken around the temporal position of said at least one heartbeat; normalizing the beat matrix such that all rows of said beat matrix have a mean of zero and a standard deviation of one; and for each of the at least one heartbeat within said segment: adding a row for said heartbeat to the real-time matrix; populating a first column of the real-time matrix with an interbeat interval between said heartbeat and an immediately preceding heartbeat; populating a second column of the real-time matrix with an interbeat interval between said heartbeat and an immediately succeeding heartbeat; populating a third column of the real-time matrix with an interval mean calculated over a pre-determined number of preceding and succeeding heartbeats relative to said heartbeat; populating a fourth column of the real-time matrix with an average of the square of the row of the normalized beat matrix corresponding to said heartbeat; populating a fifth column of the real-time matrix with an average of the square of a derivative of the row of the normalized beat matrix corresponding to said heartbeat; determining a reference beat by calculating an average between the rows of the beat matrix having the relatively lowest ratio between the fourth column and fifth column values; populating a sixth column of the real-time matrix with an average of the square of the reference beat; populating a seventh column of the real-time matrix with an average of the square of the derivative of the reference beat; populating an eighth column of the real-time matrix with a correlation coefficient between the reference beat and the row of the beat matrix corresponding to said heartbeat; populating a ninth column of the real-time matrix with a correlation coefficient between the derivatives of the reference beat and the row of the beat matrix corresponding to said heartbeat; populating a tenth column of the real-time matrix with a correlation coefficient between the squares of the reference beat and the row of the beat matrix corresponding to said heartbeat; and populating an eleventh column of the real-time matrix with a correlation coefficient between the squares of the derivatives of the reference beat and the row of the beat matrix corresponding to said heartbeat; transmitting the real-time matrix to an at least one classifier in selective communication with the at least one computing device; determining whether said segment contains arrhythmia-related heartbeats; calculating an average of the at least one interbeat interval value of said segment; and adjusting the length of an immediately succeeding segment to equal a pre-determined percentage of the calculated interbeat interval average of said segment.

24. An arrhythmia detection system for analyzing and classifying supraventricular ectopic and ventricular ectopic heartbeats of a user based on an at least one biosignal associated with heart activity of the user as captured by an at least one lead of an at least one ECG recording, the system comprising: an at least one computing device in selective communication with an at least one comparative database containing an at least one ECG recording representing a plurality of heartbeats, each said ECG recording comprising a temporal position and a beat class associated with each represented heartbeat; wherein, the at least one computing device is further configured for: constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat; dividing said at least one lead into a plurality of segments of a pre-determined temporal length; for each of the at least one segment: defining a beat matrix, each of an at least one row of said beat matrix representing a successive at least one heartbeat of said segment, and each of an at least one column of said beat matrix representing an at least one sample of said ECG recording taken around the temporal position of said at least one heartbeat; normalizing the beat matrix such that all rows of said beat matrix have a mean of zero and a standard deviation of one; and for each of the at least one heartbeat within said segment: adding a row for said heartbeat to the real-time matrix; populating a first column of the real-time matrix with an interbeat interval between said heartbeat and an immediately preceding heartbeat; populating a second column of the real-time matrix with an interbeat interval between said heartbeat and an immediately succeeding heartbeat; populating a third column of the real-time matrix with an interval mean calculated over a pre-determined number of preceding and succeeding heartbeats relative to said heartbeat; populating a fourth column of the real-time matrix with an average of the square of the row of the normalized beat matrix corresponding to said heartbeat; populating a fifth column of the real-time matrix with an average of the square of a derivative of the row of the normalized beat matrix corresponding to said heartbeat;

determining a reference beat by calculating an average between the rows of the beat matrix having the relatively lowest ratio between the fourth column and fifth column values; populating a sixth column of the real-time matrix with an average of the square of the reference beat; populating a seventh column of the real-time matrix with an average of the square of the derivative of the reference beat; populating an eighth column of the real-time matrix with a correlation coefficient between the reference beat and the row of the beat matrix corresponding to said heartbeat; populating a ninth column of the real-time matrix with a correlation coefficient between the derivatives of the reference beat and the row of the beat matrix corresponding to said heartbeat; populating a tenth column of the real-time matrix with a correlation coefficient between the squares of the reference beat and the row of the beat matrix corresponding to said heartbeat; and populating an eleventh column of the real-time matrix with a correlation coefficient between the squares of the derivatives of the reference beat and the row of the beat matrix corresponding to said heartbeat; transmitting the real-time matrix to an at least one classifier in selective communication with the at least one computing device; and determining whether said segment contains arrhythmia-related heartbeats.

25. The arrhythmia detection system according to embodiment 24, wherein the plurality of segments are non-overlapping segments of a pre-determined temporal length.

26. The arrhythmia detection system according to embodiments 24-25, wherein each of the non-overlapping segments has a temporal length of ten minutes.

27. The arrhythmia detection system according to embodiments 24-26, wherein the plurality of segments are overlapping segments of a pre-determined temporal length, with each segment being captured at a pre-determined frequency.

28. The arrhythmia detection system according to embodiments 24-27, wherein each of the overlapping segments has a temporal length of ten minutes.

29. The arrhythmia detection system according to embodiments 24-28, wherein while dividing said lead into a plurality of segments, the at least one computing device is further configured for, for each of the at least one segment: calculating an average of the at least one interbeat interval value of a given segment; and adjusting the length of an immediately succeeding segment to equal a pre-determined percentage of the calculated interbeat interval average of said given segment.

30. The arrhythmia detection system according to embodiments 24-29, wherein the at least one computing device is further configured for training the at least one classifier.

31. The arrhythmia detection system according to embodiments 24-30, wherein the at least one computing device is further configured for, for each of the at least one comparative database: for each of the at least one ECG recording contained in said comparative database: for each of the at least one lead of said ECG recording: defining a lead matrix, each of an at least one row of said lead matrix representing a successive at least one heartbeat of said ECG recording, and each of an at least one column of said lead matrix representing a characteristic of said at least one heartbeat; dividing said lead into a plurality of segments of a pre-determined temporal length; and for each of the at least one segment: defining a beat matrix, each of an at least one row of said beat matrix representing a successive at least one heartbeat of said segment, and each of an at least one column of said beat matrix representing an at least one sample of said ECG recording taken around the temporal position of said at least one heartbeat; normalizing the beat matrix such that all rows of said beat matrix have a mean of zero and a standard deviation of one; and for each of the at least one heartbeat within said segment: adding a row for said heartbeat to the lead matrix; populating a first column of the lead matrix with an interbeat interval between said heartbeat and an immediately preceding heartbeat; populating a second column of the lead matrix with an interbeat interval between said heartbeat and an immediately succeeding heartbeat; populating a third column of the lead matrix with an interval mean calculated over a pre-determined number of preceding and succeeding heartbeats relative to said heartbeat; populating a fourth column of the lead matrix with an average of the square of the row of the normalized beat matrix corresponding to said heartbeat; populating a fifth column of the lead matrix with an average of the square of a derivative of the row of the normalized beat matrix corresponding to said heartbeat; determining a reference beat by calculating an average between the rows of the beat matrix having the relatively lowest ratio between the fourth column and fifth column values; populating a sixth column of the lead matrix with an average of the square of the reference beat; populating a seventh column of the lead matrix with an average of the square of the derivative of the reference beat; populating an eighth column of the lead matrix with a correlation coefficient between the reference beat and the row of the beat matrix corresponding to said heartbeat; populating a ninth column of the lead matrix with a correlation coefficient between the derivatives of the reference beat and the row of the beat matrix corresponding to said heartbeat; populating a tenth column of the lead matrix with a correlation coefficient between the squares of the reference beat and the row of the beat matrix corresponding to said heartbeat; and populating an eleventh column of the lead matrix with a correlation coefficient between the squares of the derivatives of the reference beat and the row of the beat matrix corresponding to said heartbeat; and merging each of the at least one lead matrix into a single ECG matrix associated with the at least one ECG recording contained in said comparative database.

32. The arrhythmia detection system according to embodiments 24-31, wherein the at least one computing device is further configured for, for each of the at least one ECG recording contained in said comparative database: resampling said ECG recording to an appropriate common sampling rate; converting the temporal position associated with each represented heartbeat of said ECG recording to time units; and converting the beat class associated with each represented heartbeat of said ECG recording to a binary value.

33. The arrhythmia detection system according to embodiments 24-32, wherein while resampling said ECG recording to an appropriate common sampling rate, the at least one computing device is further configured for resampling said ECG recording to 250 Hz.

34. The arrhythmia detection system according to embodiments 24-33, wherein while converting the beat class associated with each represented heartbeat of said ECG recording to a binary value, the at least one computing device is further configured for: upon determining that a given heartbeat has a supraventricular origin, assigning the beat class for said heartbeat a binary value of zero; and upon determining that a given heartbeat has a ventricular origin, assigning the beat class for said heartbeat a binary value of one.

35. The arrhythmia detection system according to embodiments 24-34, wherein the at least one computing device is further configured for, for each of the at least one ECG recording contained in said comparative database, filtering said ECG recording to remove any unwanted high frequency noise and to correct a baseline of said ECG recording.

36. The arrhythmia detection system according to embodiments 24-35, wherein while filtering said ECG recording, the at least one computing device is further configured for filtering said ECG recording using a second order Butterworth high-pass filter with a cutoff frequency of 0.5 Hz and a finite impulse response filter of 12th order with 35 Hz at 3 decibels.

37. The arrhythmia detection system according to embodiments 24-36, wherein the at least one computing device is further configured for, for each of the at least one ECG recording contained in said comparative database, adjusting the temporal position associated with each represented heartbeat of said ECG recording to be at the largest local extrema in a QRS complex of said heartbeat.

38. The arrhythmia detection system according to embodiments 24-37, wherein while populating the third column of the real-time matrix, the at least one computing device is further configured for populating the third column with an interval mean calculated over ten preceding heartbeats and ten succeeding heartbeats relative to said heartbeat.

39. The arrhythmia detection system according to embodiments 24-38, wherein while populating the third column of the lead matrix, the at least one computing device is further configured for populating the third column with an interval mean calculated over ten preceding heartbeats and ten succeeding heartbeats relative to said heartbeat.

40. The arrhythmia detection system according to embodiments 24-39, wherein while defining the beat matrix, the at least one computing device is further configured for populating the columns of the beat matrix with at least one sample of said ECG recording taken within a window of 520 milliseconds around the temporal position of said at least one heartbeat.

41. The arrhythmia detection system according to embodiments 24-40, wherein while defining the beat matrix, the at least one computing device is further configured for populating the columns of the beat matrix with thirty samples of said ECG recording taken before the temporal position of said at least one heartbeat, and sixty samples of said ECG recording taken after the temporal position of said at least one heartbeat.

42. The arrhythmia detection system according to embodiments 24-41, wherein while populating the sixth column of the real-time matrix, the at least one computing device is further configured for populating the sixth column with an average of the square of the reference beat over a window of 520 milliseconds.

43. The arrhythmia detection system according to embodiments 24-42, wherein while populating the sixth column of the lead matrix, the at least one computing device is further configured for populating the sixth column with an average of the square of the reference beat over a window of 520 milliseconds.

44. The arrhythmia detection system according to embodiments 24-43, wherein while populating the seventh column of the real-time matrix, the at least one computing device is further configured for populating the seventh column with an average of the square of the derivative of the reference beat over a window of 520 milliseconds.

45. The arrhythmia detection system according to embodiments 24-44, wherein while populating the seventh column of the lead matrix further, the at least one computing device is further configured for populating the seventh column with an average of the square of the derivative of the reference beat over a window of 520 milliseconds.

In closing, regarding the exemplary embodiments of the present invention as shown and described herein, it will be appreciated that an arrhythmia detection system and associated methods of use are disclosed and configured for classifying supraventricular ectopic and ventricular ectopic heartbeats based on extracted data from an at least one lead of an ECG recording. Because the principles of the invention may be practiced in a number of configurations beyond those shown and described, it is to be understood that the invention is not in any way limited by the exemplary embodiments, but is generally directed to an arrhythmia detection system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for analyzing and classifying arrhythmia-related heartbeats of a user based on an at least one biosignal associated with heart activity of the user as captured by an at least one lead of an at least one ECG recording, the method comprising the steps of:
   implementing a user application residing in memory on an at least one computing device, the at least one computing device in selective communication with an at least one comparative database containing an at least one ECG recording representing a plurality of heartbeats, each said ECG recording comprising a temporal position and a beat class associated with each represented heartbeat;
   constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat;
   dividing said at least one lead into a plurality of segments of a pre-determined temporal length; and
   for each segment of the plurality of segments:
      defining a beat matrix, each of an at least one row of said beat matrix representing a successive at least one heartbeat of said segment, and each of an at least one column of said beat matrix representing an at least one sample of said ECG recording taken around the temporal position of said at least one heartbeat;
      normalizing the beat matrix such that all rows of said beat matrix have a mean of zero and a standard deviation of one; and
      for each of the at least one heartbeat within said segment:
         adding a row for said heartbeat to the real-time matrix;
         populating a first column of the real-time matrix with an interbeat interval between said heartbeat and an immediately preceding heartbeat;
         populating a second column of the real-time matrix with an interbeat interval between said heartbeat and an immediately succeeding heartbeat;
         populating a third column of the real-time matrix with an interval mean calculated over a pre-determined number of preceding and succeeding heartbeats relative to said heartbeat;
         populating a fourth column of the real-time matrix with an average of the square of the row of the normalized beat matrix corresponding to said heartbeat;
         populating a fifth column of the real-time matrix with an average of the square of a derivative of the row of the normalized beat matrix corresponding to said heartbeat;
         determining a reference beat by calculating an average between the rows of the normalized beat matrix having the relatively lowest ratio between the fourth column and fifth column values;
         populating a sixth column of the real-time matrix with an average of the square of the reference beat;
         populating a seventh column of the real-time matrix with an average of the square of the derivative of the reference beat;
         populating an eighth column of the real-time matrix with a correlation coefficient between the reference beat and the row of the beat matrix corresponding to said heartbeat;
         populating a ninth column of the real-time matrix with a correlation coefficient between the derivatives of the reference beat and the row of the beat matrix corresponding to said heartbeat;
         populating a tenth column of the real-time matrix with a correlation coefficient between the squares of the reference beat and the row of the beat matrix corresponding to said heartbeat; and
         populating an eleventh column of the real-time matrix with a correlation coefficient between the squares of the derivatives of the reference beat and the row of the beat matrix corresponding to said heartbeat;
      transmitting the real-time matrix to an at least one classifier in selective communication with the at least one computing device; and
      determining whether said segment contains arrhythmia-related heartbeats.

2. The method of claim 1, wherein the step of dividing said lead into a plurality of segments further comprises the step of dividing said lead into a plurality of non-overlapping segments of a pre-determined temporal length.

3. The method of claim 1, wherein the step of dividing said lead into a plurality of segments further comprises the step of dividing said lead into a plurality of overlapping segments of a pre-determined temporal length, with each segment being captured at a pre-determined frequency.

4. The method of claim 1, wherein the step of dividing said lead into a plurality of segments further comprises the steps of, for each segment of the plurality of segments:
   calculating an average of the at least one interbeat interval value of a given segment; and
   adjusting the length of an immediately succeeding segment to equal a pre-determined percentage of the calculated interbeat interval average of said given segment.

5. The method of claim 1, further comprising the step of training the at least one classifier.

6. The method of claim 5, further comprising the steps of, for each of the at least one comparative database:
   for each of the at least one ECG recording contained in said comparative database:
      for each of the at least one lead of said ECG recording:
         defining a lead matrix, each of an at least one row of said lead matrix representing a successive at least one heartbeat of said ECG recording, and each of an at least one column of said lead matrix representing a characteristic of said at least one heartbeat;

dividing said lead into a plurality of segments of a pre-determined temporal length; and for each segment of the plurality of segments:

defining a beat matrix, each of an at least one row of said beat matrix representing a successive at least one heartbeat of said segment, and each of an at least one column of said beat matrix representing an at least one sample of said ECG recording taken around the temporal position of said at least one heartbeat;

normalizing the beat matrix such that all rows of said beat matrix have a mean of zero and a standard deviation of one; and for each of the at least one heartbeat within said segment:

adding a row for said heartbeat to the lead matrix;

populating a first column of the lead matrix with an interbeat interval between said heartbeat and an immediately preceding heartbeat;

populating a second column of the lead matrix with an interbeat interval between said heartbeat and an immediately succeeding heartbeat;

populating a third column of the lead matrix with an interval mean calculated over a pre-determined number of preceding and succeeding heartbeats relative to said heartbeat;

populating a fourth column of the lead matrix with an average of the square of the row of the normalized beat matrix corresponding to said heartbeat;

populating a fifth column of the lead matrix with an average of the square of a derivative of the row of the normalized beat matrix corresponding to said heartbeat;

determining a reference beat by calculating an average between the rows of the normalized beat matrix having the relatively lowest ratio between the fourth column and fifth column values;

populating a sixth column of the lead matrix with an average of the square of the reference beat;

populating a seventh column of the lead matrix with an average of the square of the derivative of the reference beat;

populating an eighth column of the lead matrix with a correlation coefficient between the reference beat and the row of the beat matrix corresponding to said heartbeat;

populating a ninth column of the lead matrix with a correlation coefficient between the derivatives of the reference beat and the row of the beat matrix corresponding to said heartbeat;

populating a tenth column of the lead matrix with a correlation coefficient between the squares of the reference beat and the row of the beat matrix corresponding to said heartbeat; and populating an eleventh column of the lead matrix with a correlation coefficient between the squares of the derivatives of the reference beat and the row of the beat matrix corresponding to said heartbeat; and merging each of the at least one lead matrix into a single ECG matrix associated with the at least one ECG recording contained in said comparative database.

7. The method of claim 6, further comprising the steps of, for each of the at least one ECG recording contained in said comparative database:

resampling said ECG recording to an appropriate common sampling rate;

converting the temporal position associated with each represented heartbeat of said ECG recording to time units; and converting the beat class associated with each represented heartbeat of said ECG recording to a binary value.

8. The method of claim 7, wherein the step of converting the beat class associated with each represented heartbeat of said ECG recording to a binary value, further comprises the steps of:

upon determining that a given heartbeat has a supraventricular origin, assigning the beat class for said heartbeat a binary value of zero; and upon determining that a given heartbeat has a ventricular origin, assigning the beat class for said heartbeat a binary value of one.

9. The method of claim 1, wherein the step of populating the third column of the real-time matrix, further comprising the step of populating the third column with an interval mean calculated over ten preceding heartbeats and ten succeeding heartbeats relative to said heartbeat.

10. The method of claim 6, wherein the step of populating the third column of the lead matrix, further comprising the step of populating the third column with an interval mean calculated over ten preceding heartbeats and ten succeeding heartbeats relative to said heartbeat.

11. The method of claim 1, wherein the step of defining the beat matrix further comprises the step of populating the columns of the beat matrix with at least one sample of said ECG recording taken within a window of 520 milliseconds around the temporal position of said at least one heartbeat.

12. The method of claim 11, wherein the step of defining the beat matrix further comprises the step of populating the columns of the beat matrix with thirty samples of said ECG recording taken before the temporal position of said at least one heartbeat, and sixty samples of said ECG recording taken after the temporal position of said at least one heartbeat.

13. The method of claim 6, wherein the step of defining the beat matrix further comprises the step of populating the columns of the beat matrix with at least one sample of said ECG recording taken within a window of 520 milliseconds around the temporal position of said at least one heartbeat.

14. The method of claim 13, wherein the step of defining the beat matrix further comprises the step of populating the columns of the beat matrix with thirty samples of said ECG recording taken before the temporal position of said at least one heartbeat, and sixty samples of said ECG recording taken after the temporal position of said at least one heartbeat.

15. The method of claim 1, wherein the step of populating the sixth column of the real-time matrix further comprises the step of populating the sixth column with an average of the square of the reference beat over a window of 520 milliseconds.

16. The method of claim 6, wherein the step of populating the sixth column of the lead matrix further comprises the step of populating the sixth column with an average of the square of the reference beat over a window of 520 milliseconds.

17. The method of claim 1, wherein the step of populating the seventh column of the real-time matrix further comprises the step of populating the seventh column with an average of the square of the derivative of the reference beat over a window of 520 milliseconds.

18. The method of claim 6, wherein the step of populating the seventh column of the lead matrix further comprises the step of populating the seventh column with an average of the square of the derivative of the reference beat over a window of 520 milliseconds.

19. A method for analyzing and classifying arrhythmia-related heartbeats of a user based on an at least one biosignal associated with heart activity of the user as captured by an at least one lead of an at least one ECG recording, the method comprising the steps of:
  implementing a user application residing in memory on an at least one computing device, the at least one computing device in selective communication with an at least one comparative database containing an at least one ECG recording representing a plurality of heartbeats, each said ECG recording comprising a temporal position and a beat class associated with each represented heartbeat;
  constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat;
  dividing said at least one lead into a plurality of segments of a pre-determined temporal length; and
  for each segment of the plurality of segments:
    defining a beat matrix, each of an at least one row of said beat matrix representing a successive at least one heartbeat of said segment, and each of an at least one column of said beat matrix representing an at least one sample of said ECG recording taken around the temporal position of said at least one heartbeat;
    normalizing the beat matrix such that all rows of said beat matrix have a mean of zero and a standard deviation of one; and
    for each of the at least one heartbeat within said segment:
      adding a row for said heartbeat to the real-time matrix;
      populating a first column of the real-time matrix with an interbeat interval between said heartbeat and an immediately preceding heartbeat;
      populating a second column of the real-time matrix with an interbeat interval between said heartbeat and an immediately succeeding heartbeat;
      populating a third column of the real-time matrix with an interval mean calculated over a pre-determined number of preceding and succeeding heartbeats relative to said heartbeat;
      populating a fourth column of the real-time matrix with an average of the square of the row of the normalized beat matrix corresponding to said heartbeat;
      populating a fifth column of the real-time matrix with an average of the square of a derivative of the row of the normalized beat matrix corresponding to said heartbeat;
      determining a reference beat by calculating an average between the rows of the normalized beat matrix having the relatively lowest ratio between the fourth column and fifth column values;
      populating a sixth column of the real-time matrix with an average of the square of the reference beat;
      populating a seventh column of the real-time matrix with an average of the square of the derivative of the reference beat;
      populating an eighth column of the real-time matrix with a correlation coefficient between the reference beat and the row of the beat matrix corresponding to said heartbeat;
      populating a ninth column of the real-time matrix with a correlation coefficient between the derivatives of the reference beat and the row of the beat matrix corresponding to said heartbeat;
      populating a tenth column of the real-time matrix with a correlation coefficient between the squares of the reference beat and the row of the beat matrix corresponding to said heartbeat; and
      populating an eleventh column of the real-time matrix with a correlation coefficient between the squares of the derivatives of the reference beat and the row of the beat matrix corresponding to said heartbeat;
    transmitting the real-time matrix to an at least one classifier in selective communication with the at least one computing device;
    determining whether said segment contains arrhythmia-related heartbeats;
    calculating an average of the at least one interbeat interval value of said segment; and
    adjusting the length of an immediately succeeding segment to equal a pre-determined percentage of the calculated interbeat interval average of said segment.

20. An arrhythmia detection system for analyzing and classifying supraventricular ectopic and ventricular ectopic heartbeats of a user based on an at least one biosignal associated with heart activity of the user as captured by an at least one lead of an at least one ECG recording, the system comprising:
  an at least one computing device in selective communication with an at least one comparative database containing an at least one ECG recording representing a plurality of heartbeats, each said ECG recording comprising a temporal position and a beat class associated with each represented heartbeat;
  wherein, the at least one computing device is further configured for:
    constructing a real-time matrix corresponding to the at least one lead associated with heart activity of the user, each of an at least one row of said real-time matrix representing a successive at least one heartbeat of said at least one lead, and each of an at least one column of said real-time matrix representing a characteristic of said at least one heartbeat;
    dividing said at least one lead into a plurality of segments of a pre-determined temporal length; and
    for each segment of the plurality of segments:
      defining a beat matrix, each of an at least one row of said beat matrix representing a successive at least one heartbeat of said segment, and each of an at least one column of said beat matrix representing an at least one sample of said ECG recording taken around the temporal position of said at least one heartbeat;
      normalizing the beat matrix such that all rows of said beat matrix have a mean of zero and a standard deviation of one; and for each of the at least one heartbeat within said segment:
adding a row for said heartbeat to the real-time matrix;
populating a first column of the real-time matrix with an interbeat interval between said heartbeat and an immediately preceding heartbeat;
populating a second column of the real-time matrix with an interbeat interval between said heartbeat and an immediately succeeding heartbeat;
populating a third column of the real-time matrix with an interval mean calculated over a predetermined number of preceding and succeeding heartbeats relative to said heartbeat;
populating a fourth column of the real-time matrix with an average of the square of the row of the normalized beat matrix corresponding to said heartbeat;
populating a fifth column of the real-time matrix with an average of the square of a derivative of the row of the normalized beat matrix corresponding to said heartbeat;
determining a reference beat by calculating an average between the rows of the normalized beat matrix having the relatively lowest ratio between the fourth column and fifth column values;
populating a sixth column of the real-time matrix with an average of the square of the reference beat;
populating a seventh column of the real-time matrix with an average of the square of the derivative of the reference beat;
populating an eighth column of the real-time matrix with a correlation coefficient between the reference beat and the row of the beat matrix corresponding to said heartbeat;
populating a ninth column of the real-time matrix with a correlation coefficient between the derivatives of the reference beat and the row of the beat matrix corresponding to said heartbeat;
populating a tenth column of the real-time matrix with a correlation coefficient between the squares of the reference beat and the row of the beat matrix corresponding to said heartbeat; and
populating an eleventh column of the real-time matrix with a correlation coefficient between the squares of the derivatives of the reference beat and the row of the beat matrix corresponding to said heartbeat;
transmitting the real-time matrix to an at least one classifier in selective communication with the at least one computing device; and
determining whether said segment contains arrhythmia-related heartbeats.

* * * * *